United States Patent
Schroeter

(10) Patent No.: US 10,627,533 B2
(45) Date of Patent: Apr. 21, 2020

(54) REDUCING DRIFT EFFECTS OF SCINTILLATOR DETECTORS BY LIGHT IRRADIATION

(71) Applicant: Siemens Healthcare GmbH, Erlangen (DE)

(72) Inventor: Christian Schroeter, Bamberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 654 days.

(21) Appl. No.: 15/194,665

(22) Filed: Jun. 28, 2016

(65) Prior Publication Data
US 2017/0010366 A1    Jan. 12, 2017

(30) Foreign Application Priority Data
Jul. 9, 2015 (DE) .......... 10 2015 212 881

(51) Int. Cl.
*G01T 1/208* (2006.01)
*A61B 6/00* (2006.01)

(52) U.S. Cl.
CPC .............. *G01T 1/208* (2013.01); *A61B 6/585* (2013.01)

(58) Field of Classification Search
CPC ..... G01T 1/208; G01T 1/2018; G01T 1/2023; G01T 1/20; A61B 6/585
See application file for complete search history.

(56) References Cited

U.S. PATENT DOCUMENTS

| 3,179,801 A | 4/1965 | Scherbatskoy |
| 7,049,598 B1* | 5/2006 | Jordanov ............... G01T 1/208 250/207 |
| 2005/0269513 A1 | 12/2005 | Ianakiev et al. |
| 2007/0007460 A1* | 1/2007 | Hochstetler ............ G01T 1/20 250/370.11 |
| 2016/0124094 A1* | 5/2016 | Melcher .................. G01T 1/202 250/365 |

FOREIGN PATENT DOCUMENTS

| DE | 102006033716 A1 | 2/2008 |
| WO | WO-2006015608 A1 | 2/2006 |
| WO | WO-2014201234 A1 | 12/2014 |

OTHER PUBLICATIONS

Translation of DE 102006033716. (Year: 2008).*

* cited by examiner

*Primary Examiner* — Chih-Cheng Kao
(74) *Attorney, Agent, or Firm* — Harness, Dickey & Pierce, P.L.C.

(57) ABSTRACT

A detector is disclosed for detecting X-ray and/or gamma radiation, including a scintillator element for converting the X-ray and/or gamma radiation into light. The scintillator element has at least one side surface, an upper side and a lower side, a first photodiode on the lower side of the scintillator element. The detector further includes an electronic evaluation device, a light source designed to illuminate the scintillator element, and a light-impermeable housing which surrounds the scintillator element, the first photodiode, the electronic evaluation device and the light source.

23 Claims, 4 Drawing Sheets

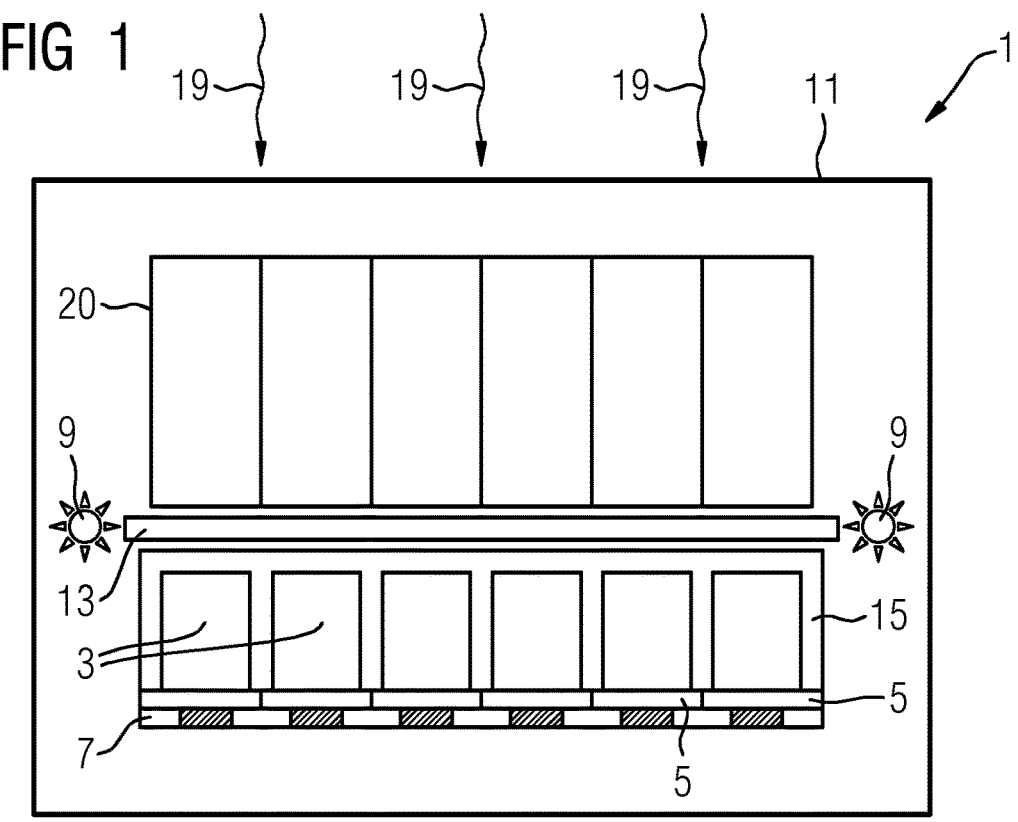
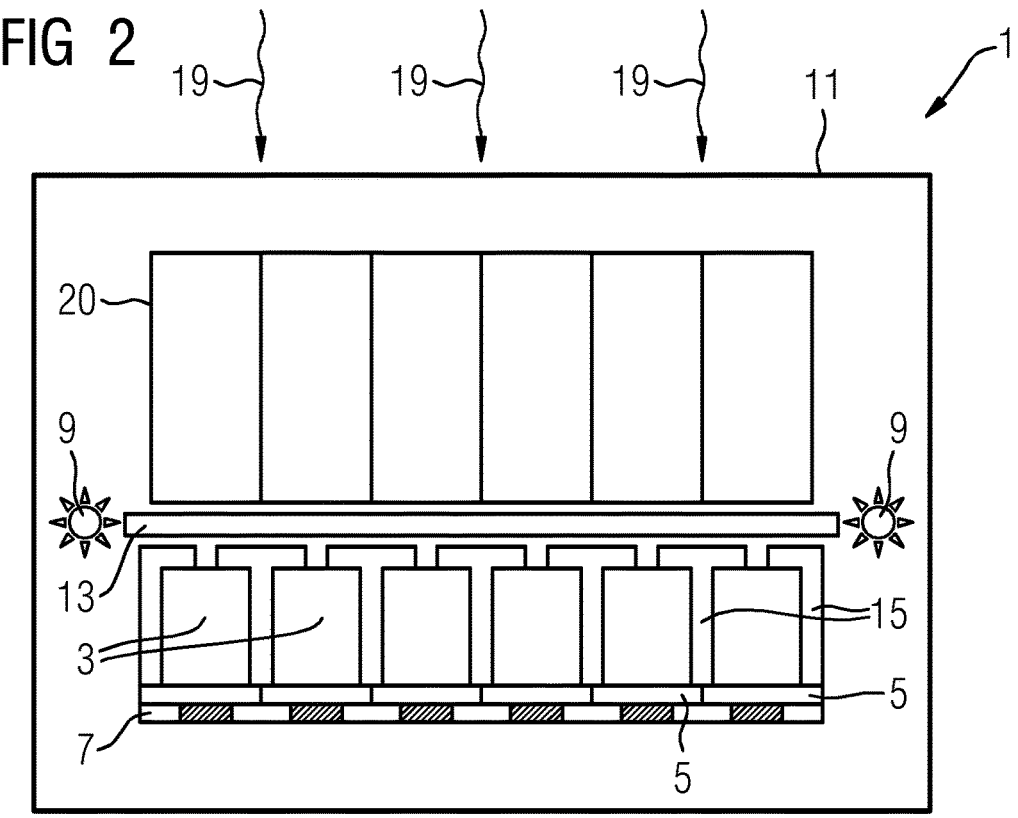

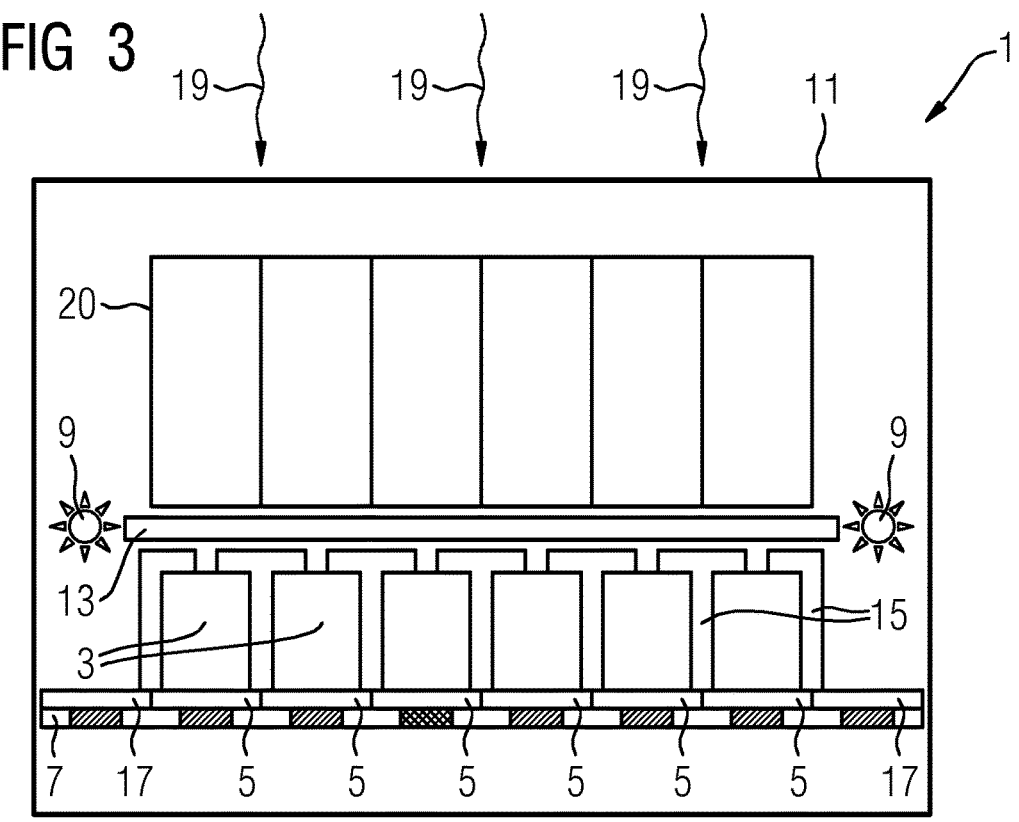
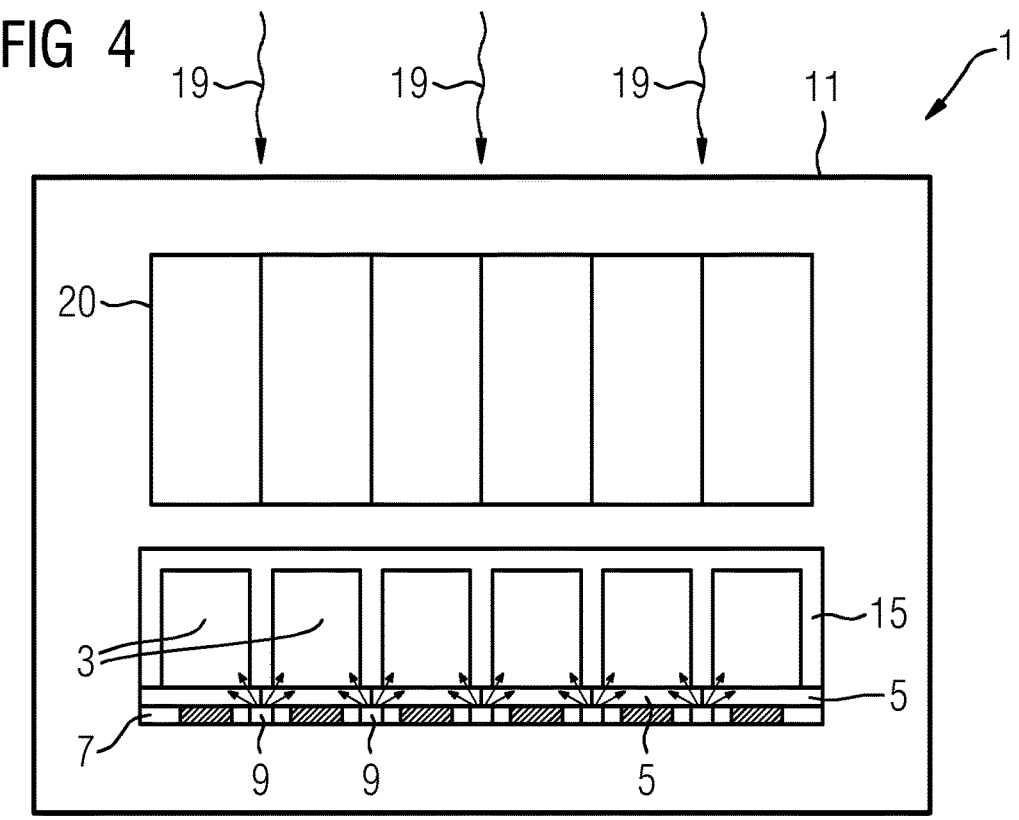

REDUCING DRIFT EFFECTS OF SCINTILLATOR DETECTORS BY LIGHT IRRADIATION

PRIORITY STATEMENT

The present application hereby claims priority under 35 U.S.C. § 119 to German patent application number DE 102015212881.4 filed Jul. 9, 2015, the entire contents of which are hereby incorporated herein by reference.

FIELD

At least one embodiment of the invention generally relates to a detector for detecting X-ray and/or gamma radiation, to a method for determining a state of a scintillator element of a detector and/or to a medical device.

BACKGROUND

Detectors are used, for example, in computer tomographs, angiography machines or radiography equipment to convert X-ray radiation into electrical signals which act as the basis for calculating two- or three-dimensional slice images of a patient to be examined. Scintillators are often used for detecting X-ray or gamma radiation. Scintillators are used, in particular, in medical X-ray imaging in an energy range up to 1 MeV.

What are referred to as indirectly converting detectors, what are known as scintillator detectors, are conventionally used, in which the X-ray or gamma rays are converted into electrical signals in two stages. In a first stage the X-ray or gamma quanta are absorbed in a scintillator element and converted into optically visible light. This effect is called luminescence. The light excited by luminescence is then converted in a second stage by a first photodiode optically coupled to the scintillator element into an electrical signal, read out by an electronic evaluation or readout device and then forwarded to an arithmetic unit.

In many applications, for example in computerized tomography or angiography, very high photon fluxes are used to achieve very fast imaging, for example of moving organs. A change in the response function of the detector can occur in the case of high photon fluxes. This change is often called drift. Passivation of light centers occurs as a result of irradiation with X-ray or gamma radiation, wherein the light centers are put into electronic states in which they can no longer contribute to luminescence. The electronic states can dissipate again with time. The electronic states can dissipate with different time constants which can be in the region of a few seconds to several days. Temporarily there is a changed response function which brings about artifacts and/or inaccurate quantitative scans in the imaging. Changes in the response function of the detector can therefore occur within a scan as well as after a large number of scans.

The state of the scintillator element can also have an effect on the transmission properties with some scintillator materials, for example $Gd_2O_2S$ (GOS). In particular, the transmission of a specific wavelength can be changed under the influence of X-ray radiation. Clouding of the scintillator material can occur, and this can lead to reduced transmission. With other scintillator materials, for example CsI, the transmission can be increased under the influence of X-ray radiation.

Previously calibrations have been performed without object or with a known object suitable for calibration purposes between radiation source and detector in order to ascertain changes in the response function. In this case the radiation source is operated with known parameters and the detector response measured. The changes in the response function of the detector can be used for correcting scan values or for correction during image reconstruction. The use of X-ray or gamma radiation is required for this method. Calibration cannot take place during patient treatment therefore, for example between scans, during a change of patient or immediately before or after a scan. This method of calibration is therefore typically carried out daily. Despite these calibrations artifacts can occur in the imaging and inaccurate quantitative analyses can occur since changes in the response function of the detector with time constants of less than one day cannot be taken into account.

SUMMARY

The inventor has found that changes in the response function, in particular with time constants of less than one day, cannot be taken into account using the previous calibration methods. The use of X-ray or gamma radiation prevents repeated or frequent scanning of the response function during patient treatment.

Embodiments of the invention disclose a detector, a method for determining a state of a scintillator element and a medical device which enable stabilization of the response function of an indirect conversion detector having a scintillator element for converting the X-ray radiation or gamma radiation into light, wherein stabilization or correction of the calibration can be carried out during patient treatment.

Embodiments of the invention include a detector, a method for determining a state of a scintillator element and a medical device.

In at least one embodiment, the inventor is proposing to stabilize the detector response of a detector for detecting X-ray and/or gamma radiation, having a scintillator element for converting the X-ray and/or gamma radiation into light by illuminating the scintillator element using a defined quantity of light and determining the state of the scintillator element or carrying out a correction of the calibration.

At least one embodiment of the invention relates to a detector for detecting X-ray and/or gamma radiation, having a scintillator element for converting the X-ray and/or gamma radiation into light, wherein the scintillator element has at least one side surface, an upper side and a lower side, a first photodiode at the lower side of the scintillator element, an electronic evaluation device, a light source, wherein the light source is designed to illuminate the scintillator element, and a light-impermeable housing which surrounds the scintillator element, the first photodiode, the electronic evaluation device and the light source. The light-impermeable housing can be designed, for example, as a semi-transparent reflector layer.

At least one embodiment of the invention relates to a method for determining a state of a scintillator element of an inventive detector having steps a) and b). Step a) comprises illuminating the scintillator element with a defined quantity of light. Step b) comprises determining the state of the scintillator element.

Embodiments of the invention also relate to a medical device having at least one embodiment of an inventive detector.

Advantages of embodiments of the inventive detector and embodiments of the inventive method can be transferred to the medical device.

BRIEF DESCRIPTION OF THE DRAWINGS

Example embodiments of the invention will be illustrated in more detail below with reference to drawings, in which:

FIG. 1 schematically shows a diagram of an embodiment of an inventive detector;

FIG. 2 schematically shows a diagram of an embodiment of an inventive detector having openings in the reflector material at the upper side of the scintillator element;

FIG. 3 schematically shows a diagram of an embodiment of an inventive detector having the second photodiode;

FIG. 4 schematically shows a diagram of an embodiment of an inventive detector having light sources integrated in the electronic evaluation device;

DETAILED DESCRIPTION OF THE EXAMPLE EMBODIMENTS

Figure 5:
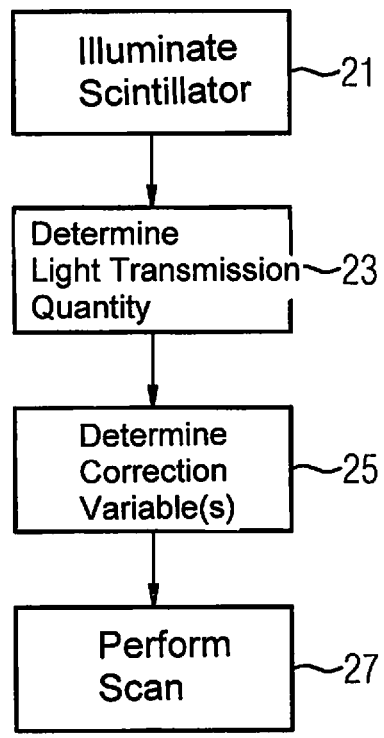
FIG. 5 schematically shows a diagram of an embodiment of an inventive method for ascertaining a state of the scintillator element.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a detector for detecting X-ray and/or gamma radiation, having a scintillator element for converting the X-ray and/or gamma radiation into light, wherein the scintillator element has at least one side surface, an upper side and a lower side, a first photodiode at the lower side of the scintillator element, an electronic evaluation device, a light source, wherein the light source is designed to illuminate the scintillator element, and a light-impermeable housing which surrounds the scintillator element, the first photodiode, the electronic evaluation device and the light source. The light-impermeable housing can be designed, for example, as a semi-transparent reflector layer.

In an embodiment, the detector has a scintillator element, a first photodiode, an electronic evaluation device, a light source and a light-impermeable housing. In a preferred embodiment the X-ray or gamma radiation firstly strikes the scintillator element and is converted there into a quantity of light. A quantity of light is registered in the following first photodiode and a scan value for the quantity of light is forwarded to the electronic evaluation device.

In a further embodiment the detector can have at least one detector module, wherein the detector module can comprise a plurality of detection elements. One detection element comprises a unit comprising scintillator element, first photodiode and electronic evaluation device. The detection elements can be in a two-dimensional arrangement.

The scintillator element has at least one side surface, an upper side and a lower side. The upper side advantageously points toward the X-ray or gamma radiation source and the lower side rests on the side of the scintillator element remote from the X-ray or gamma radiation source. The volume of the scintillator element is also advantageously surrounded by at least one side surface. In a preferred embodiment the upper side and the lower side of the scintillator element can be in the form of a rectangular or square base area, and a plurality of side surfaces may be present accordingly. In one embodiment having a plurality of detection elements the scintillator elements are arranged side by side such that the side surfaces of the adjacent scintillator elements run substantially parallel.

The detector can have a collimator, for example in the form of a one- or two-dimensional scattered radiation grid, wherein the collimator is arranged between the radiation source and the upper side of the scintillator element.

The detector can detect X-ray or gamma radiation in the energy range of 1 keV to 1 MeV; a preferred energy range lies in the range of 10 keV to 200 keV.

The lower side of the scintillator element is advantageously connected in a light-conducting manner to a first photodiode. The first photodiode is designed such that the light excited by luminescence can be detected and a quantity of light can be determined. In one embodiment the first photodiode can be contained in a substrate, wherein the first photodiode can be, for example, smaller than the area of the lower side of the scintillator element and, for example, the first photodiode can be arranged centrally below the scintillator element.

The value determined for the quantity of light is forwarded to the electronic evaluation device. The electronic evaluation device can be designed, for example as an ASIC (Application Specific Integrated Circuit).

The light source is arranged such that it can advantageously illuminate the scintillator element. Additional optical elements can be used for illumination of the scintillator element. The scintillator element can be illuminated directly or indirectly by the light source.

A light-impermeable housing surrounds the scintillator element, the first photodiode, the electronic evaluation device and the light source, so, in particular, the photodiode and the scintillator element are advantageously shielded from external light effects. The light-impermeable housing can be designed in one part or in several parts, and can have openings, for example for cable routing, or at the abutting points or surfaces.

Since the scintillator element and photodiode are shielded from external light effects, the light source is advantageously capable of illuminating the scintillator element with a defined quantity of light. Effects from other light sources outside of the light-impermeable housing are avoided. With the aid of the defined quantity of light the state of the scintillator element can be determined, for example, by determining the transmission or luminescence of the scintillator element or by producing a predetermined state of the scintillator element. The information obtained therefrom about the state of the scintillator element can advantageously be used for correcting the response function of the detector. The correction can be applied to the scan values or be taken into account within the framework of image reconstruction. Reproducible scan values or reproducible reconstructed images can be achieved with the detector as a result. Alternatively, the state of the scintillator can be established even before recording the daily calibration due to the establishment of a predetermined state by way of irradiation with light of a suitable wavelength. Since the detector is then already in a predetermined state additional changes can be reduced by way of X-ray radiation. The state of the scintillator element can be brought about by illumination with a defined quantity of light.

At least one embodiment of the invention relates to a method for determining a state of a scintillator element of an inventive detector having steps a) and b). Step a) comprises illuminating the scintillator element with a defined quantity of light. Step b) comprises determining the state of the scintillator element.

In an embodiment, step a) comprises illuminating the scintillator element with the aid of the light source. The light source illuminates the scintillator element with a defined quantity of light which is set by way of a controller at a predetermined value. The defined quantity of light advantageously enables reproducible boundary conditions for step b) for determining the state of the scintillator element.

Determining the state of the scintillator element can comprise ascertaining the state of the scintillator element or establishing or bringing about or setting a specific state.

The state of the scintillator element can be determined by ascertaining the transmission or luminescence. The first photodiode is advantageously used for ascertaining a quantity of light, wherein the ascertained quantity of light is a measure of the transmission or luminescence of the scintillator element.

The determined state of the scintillator element can advantageously be used to simplify calibration of the detector, to achieve an increase in the stability of the calibration, reproducible scan values or reproducible reconstructed images.

An embodiment of the inventive method is advantageously capable of recognizing, correcting or preventing changes in the response function of the detector. The image quality can advantageously be improved, in particular when using adjacent detector modules having a different change in the response function. Laborious sorting of detector modules can advantageously be avoided during production. Using embodiments of the inventive method, scintillator materials, for example CsI or compound converters, can be used which could not previously be employed in medical imaging having high photon fluxes, for example in computerized tomography, owing to changes in the response function. In embodiments of the present invention, inexpensive detectors can advantageously be used in medical imaging having high photon fluxes, wherein embodiments of the inventive method reduce or prevent changes in the response function of the detector.

Embodiments of the invention also relate to a medical device having at least one embodiment of an inventive detector.

Advantages of embodiments of the inventive detector and embodiments of the inventive method can be transferred to the medical device.

In particular, embodiments of the inventive detector or embodiments of the inventive method achieves an advantageous, improved reproducibility for imaging with the medical device. The advantages include, for example, a reduction of artifacts in the reconstructed images or an improvement in the quantitative scans.

According to one embodiment of the inventive detector the light source is designed to emit photons from the light source having a wavelength less than an excitation wavelength of the scintillator element.

One wavelength which is emitted by the light source can advantageously be chosen so the one wavelength is shorter than the excitation wavelength for luminescence. The light source can advantageously excite the scintillator element for luminescence as a result. The one wavelength can lie, for example, in the ultraviolet range.

According to one embodiment of the inventive detector, the light source is designed to emit photons having a wavelength which can be detected by the first photodiode.

The light source can advantageously emit photons having a wavelength which can be detected by the first photodiode in order to be able to determine the transmission. For example, the wavelength can be chosen such that the absorption in the scintillator element is as strongly pronounced as possible. The photons which are not absorbed can then advantageously be registered by the first photodiode. A scan value can advantageously be ascertained for the transmission. For example, the wavelength can be chosen such that it lies in a range in which the change in the state of the scintillator element in respect of absorption is greatest. In the case of GOS this wavelength is, for example, 511 nm. This corresponds to the absorption maximum of GOS.

According to one embodiment of the inventive detector, the detector has an optical element for uniform illumination of at least one section of the scintillator element.

An optical element can advantageously ensure substantially uniform illumination of the scintillator element or uniform illumination of at least one section of the scintillator element. The light source can advantageously illuminate the scintillator element indirectly. The arrangement of the light source can thereby also be such that the light source is, for example, laterally upwardly offset from the scintillator element. The optical element can be located above the upper side of the scintillator element or to the side, next to a gap between collimator and scintillator element. The light source can advantageously be located outside of the beam path between X-ray or gamma radiation source and scintillator element. A lens, diffusor or a reflecting surface, for example, can be used as the optical element. A transparent film or acrylic glass, for example, can be used as the diffusor. At the side remote from the scintillator element the diffusor is designed such that the defined quantity of light is homogeneously coupled out over the entire surface of the diffusor. At the side remote from the scintillator element the diffusor can have a reflective layer, for example a film or a paint. To achieve coupling-out of the light in particular in the direction of the scintillator material, the surface facing the scintillator element can be roughened or have scattering bodies in the diffusor material.

According to one embodiment of the inventive detector, the detector has a filter between the scintillator element and the first photodiode which is permeable for the wavelength of the light source.

A filter can be used which advantageously blocks the wavelength emitted by the light source and transmits the wavelength of the luminescence light. An effect of the light source on the first photodiode can be prevented or reduced as a result.

According to one embodiment of the inventive detector the light source is arranged such that the upper side or the lower side of the scintillator element can be illuminated.

The light source can advantageously illuminate the scintillator element at the upper side or lower side, so, for example, further scintillator elements can be arranged next to the scintillator element. In one embodiment for ascertaining the transmission an illumination of the scintillator element from above is particularly advantageous. In a further embodiment for ascertaining the luminescence or for establishing a predetermined state, illumination of the scintillator element at the upper or lower side can be advantageous.

According to one embodiment of the inventive detector the at least one side surface and/or the upper side of the scintillator element is at least partially covered by a reflector material.

The reflector material can advantageously cover the at least one side surface and/or the upper side of the scintillator element in order to shield the scintillator element from lateral illumination, for example luminescence light from an adjacent scintillator element or the light source, or an undesirable illumination at the upper side, for example in the case of illumination due to the light source at the lower side of the scintillator element, and to achieve an optimum light yield of the luminescence light. Different reflector materials can be used, with, for example, a different reflector material being used for the side surface and the upper side respectively. For example, what is known as a top reflector can be used at the upper side to achieve an optimally high light intensity at the first photodiode.

Typical materials for top reflectors have a transmission since the thickness is limited due to the absorption of X-ray radiation. For example, a Hostaphan film having a thickness of 50 µm can be used which has a transmission of about 25%. A transmission of the reflector material of, for example, 25% can advantageously be used for illumination of the scintillator element by a light source at the upper side of the scintillator element.

In an alternative embodiment the reflector material at the upper side of the scintillator element can have a structuring, for example in the form of openings or reduced thickness of the reflector material, so the surface of the scintillator element is only partially covered and the structuring advantageously enables illumination of the scintillator element from above. In the case of scintillator elements having a high light yield, for example CsI, covering of the upper side of the scintillator element with a reflector material can be dispensed with and the scintillator element can be illuminated with the light source particularly advantageously from above.

According to one embodiment of the inventive detector the light source is integrated in the electronic evaluation device.

The light source can advantageously be incorporated by the electronic evaluation device, so the scintillator element is illuminated at the lower side. An LED, for example, can be used as the light source. The light source is advantageously associated with the scintillator element. Optical elements above the upper side of the scintillator element can advantageously be omitted.

According to one embodiment of the inventive detector the detector has a second photodiode and the second photodiode can be illuminated by the light source, for example, in that the light source and the second photodiode are arranged in relation to each other such that the second photodiode can be directly or indirectly illuminated by the light source.

The second photodiode can be illuminated by the light source and can advantageously be used for checking the reliability of the first photodiode or the light source. The second photodiode can be located for example next to the first photodiode, with no scintillator element being located above the second photodiode. An additional filter can be used upstream of the second photodiode.

With at least one embodiment of the inventive method it is necessary to ascertain or prevent changes in the transmission or luminescence in the range of, for example, less than 1 percent. A second photodiode can ascertain or ensure the reproducibility of illumination with a defined quantity of light in order to reduce the effect of changes in the defined quantity of light.

For example, a second photodiode can be used which is identical in terms of construction to the first photodiode in order to advantageously prevent effects from the characteristics of the second photodiode compared to the first photodiode. It can be advantageous for the first photodiode and the second photodiode to have the same material properties and identical temperature conditions to prevent effects of the scan using the second photodiode on the evaluation of the reproducibility of the defined quantity of light.

According to one embodiment of the inventive detector, the detector also comprises a controller with which the light source can be controlled to emit a defined quantity of light.

The controller can advantageously meter the quantity of light. For example, at least one embodiment of the inventive method can advantageously be repeated with a reproducible, defined quantity of light. The method can thereby enable advantageous monitoring of the state of the scintillator element and reproducibility of the image quality of the medical device over a period.

According to one embodiment of the inventive detector the first photodiode or/and the second photodiode is/are connected to an evaluation device.

The evaluation device can advantageously perform the evaluation of the quantity of light ascertained by the first photodiode or second photodiode. For the existing state of the scintillator element the evaluation determines, for example in respect of the transmission or luminescence, a correction variable, for example a correction factor or an amplification factor.

According to at least one embodiment of the inventive method, the step of determining the state of the scintillator element comprises establishing a predetermined state by illumination by way of the defined quantity of light.

A state can be established or brought about by pre-irradiation of the scintillator element. The defined quantity of light used in step a) can establish an advantageous predetermined state of the scintillator element. The predetermined state can be established before calibration using X-ray radiation and before scans. The defined quantity of light can correspond to a quantity of light which establishes a state corresponding to the state following irradiation of X-ray radiation.

The light source is advantageously designed such that the luminescence excited by the light source is comparable to luminescence excited by X-ray or gamma radiation. In particular, a state is advantageously that which lies in a saturation range in respect of polarization, transmission or luminescence. In the predetermined state the state of the scintillator element can remain in the predetermined state under the effect of von X-ray or gamma radiation. A change in the detector response due to the establishment of the predetermined state can advantageously be prevented.

A wavelength of the defined quantity of light can advantageously be chosen so the one wavelength is shorter than the excitation wavelength for luminescence. The wavelength can lie, for example, in the ultraviolet range. An LED, for example, can be used as the light source. In addition, a filter can advantageously be used which blocks the wavelengths emitted by the light source and transmits the wavelength of the luminescence light.

According to at least one embodiment of the inventive method, the step of determining the state of the scintillator element comprises a step of ascertaining the state by way of the quantity of light.

For ascertaining the transmission of the scintillator element a quantity of light can be ascertained and, more precisely, the portion of the defined quantity of light used in step a) for illumination which is registered by the first photodiode, with the aid of the first photodiode. This advantageously produces a scan value for the existing state of the scintillator element in respect of transmission. A wavelength of the defined quantity of light can advantageously be chosen so the absorption is strongly pronounced in the scintillator element. Furthermore, the first photodiode is advantageously capable of detecting the one wavelength. The one wavelength can be, for example, about 510 nm. This embodiment is advantageous for a scintillator element whose transmission can change due to irradiation with X-ray or gamma radiation, for example for scintillator elements containing GOS ($Gd_2O_2S$).

For ascertaining the luminescence of the scintillator element a quantity of light can be ascertained with the aid of the first photodiode, which can be converted in the scintillator element in step a) into luminescence light by excitation of the luminescence by way of irradiation with a defined quantity of light of the scintillator element. The quantity of light of the luminescence light can advantageously be registered by the first photodiode. The luminescence of the scintillator state can change under the effect of X-ray or gamma radiation. The deviation of the luminescence compared, for example, to the time of calibration can be ascertained. This advantageously produces a scan value for the existing state of the scintillator element in respect of the luminescence. A wavelength of the defined quantity of light can advantageously be chosen so the wavelength is shorter than the excitation wavelength for luminescence. The one wavelength can lie, for example, in the ultraviolet range. An LED, for example, can be used as the light source. In addition, a filter can advantageously be used which blocks the wavelength emitted by the light source and transmits the wavelength of the luminescence light. This embodiment is advantageous for a scintillator element whose luminescence can change due to irradiation with X-ray or gamma radiation.

The state of the scintillator element can advantageously be ascertained in the scanning breaks or in periods without irradiation of X-ray or gamma radiation during the scan. Illumination of the scintillator element and ascertaining the state can occur, for example, directly after or before calibration using X-ray radiation in order to detect the state of the scintillator element at the time of calibration using X-ray radiation. Illumination of the scintillator element and ascertaining the state can be repeated, for example, in the scanning breaks or in periods without irradiation of X-ray or gamma radiation during the scan, and a deviation in the transmission or luminescence of the scintillator element compared to the time of calibration using X-ray radiation can be determined. The deviation can advantageously be used for correcting the scan data or for correcting calibration tables. The duration of illumination is preferably chosen such that the state of the scintillator element can be reliably determined. The duration of illumination can be a few milliseconds. The deviation in the state of the scintillator element constitutes a relative scan value. An inhomogeneity in the illumination of the scintillator element or a plurality of scintillator elements can advantageously be accepted in the process, so the requirements for uniform illumination can be lower, for example, with the aid of optical elements.

With the aid of the scan value for the existing state of the scintillator element in respect of transmission or luminescence, an amplification can be adjusted, the scan values can be scaled or the calibration table can be corrected, for example.

According to one embodiment of the inventive medical device the medical device is a computer tomograph.

The computer tomograph can advantageously achieve improved reproducibility for the imaging. The advantages include, for example, a reduction in artifacts in the reconstructed, also multi-dimensional, images or series of recordings or an improvement in the quantitative scans.

FIG. 1 to FIG. 4 show example embodiments of an inventive detector 1. The detector 1 comprises, for example, a detector module having a plurality of detection elements. In the side view six detection elements 3, 15, 5, 7 respectively are shown in these examples; further detection elements can extend behind them as a two-dimensional arrangement. A detection element comprises a unit composed of scintillator element 3 which is at least partially covered by a reflector material 15, first photodiode 5 and a region of the electronic evaluation device 7 which is associated with the first photodiode 5.

A first photodiode 5 is associated with the scintillator element 3 and is located at the lower side of the scintillator element 3 and is optically conductively connected, for example by an optical adhesive, to the scintillator element 3. The first photodiode 5 can be contained in a substrate, wherein the first photodiode 5 can be, for example, smaller than the area of the lower side of the scintillator element 3 and the first photodiode 5 can be arranged, for example, centrally below the scintillator element 3. The electronic evaluation device 7 is electrically conductively connected to the photodiode 5 and located at the lower side of the first photodiode 5. One region of the electronic evaluation device 7 is associated with the first photodiode 5 of this detection element. The electronic evaluation device 7 is designed, for example, as an ASIC. The X-ray radiation 19 strikes a collimator 20 which can be designed, for example, as a two-dimensional scattered radiation grid which reduces the incidence of scattered radiation on the scintillator elements 3. The walls of the collimator 20 are directed toward the gaps between adjacent scintillator elements 3.

FIG. 1 shows an example embodiment of an inventive detector 1. A detection element 3, 15, 5, 7 comprises a scintillator element 3 which is covered at the upper side and at the side surfaces by a reflector material 15. At the upper side of the scintillator element the reflector material 15 can be formed, for example, as a Hostaphan film of 50 μm thickness which can have a transmission of about 25 percent. A different reflector material 15 can also be used at the upper side and the side surfaces. Between the collimator 20 and the reflector material 15 at the upper side of the scintillator elements 3 is located an optical element 13.

Next to the optical element 13 and to the side are located light sources 9. The light from the light sources 9 can uniformly illuminate the scintillator elements 3 with the aid of the optical element 13. The optical element 13 can be formed, for example, as a diffusor or by lenses. A light-impermeable housing 11 surrounds the collimator 20, the light sources 9, the optical element 13, the scintillator elements 3 and the reflector material 15, the first photodiodes 5 and the electronic evaluation device 7. The light-impermeable housing 11 can be in one part or in several parts. The light-impermeable housing 11 shields the interior substantially from external light effects.

The light sources 9 can emit a defined quantity of light. A portion of the defined quantity of light can penetrate the reflector material 15. The defined quantity of light can be used for illumination of the scintillator elements 3 to establish a predetermined state of the scintillator element 3 or to ascertain the state of the scintillator element 3.

The FIG. 2 shows an example embodiment of an inventive detector 1 having openings in the reflector material 15 at the upper side of the scintillator element 3. A detection element 3, 15, 5, 7 comprises a scintillator element 3 which is at least partially covered at the upper side and the side surfaces by a reflector material 15. A different reflector material 15 can also be used at the upper side and the side surfaces.

The reflector material 15 has at least one opening at the upper side of the scintillator element 3 to ensure illumination of the scintillator element 3. For example, in the case of a scintillator element 3 which has a scintillator material having a high light yield, for example CsI, a very large opening of the reflector material 15 can be used at the upper side of the scintillator element 3 or the reflector material 15 can even be dispensed with at the upper side of the scintillator element 3. In the case of scintillator materials having, for example, a lower light yield a structuring of the reflector material 15 can be used at the upper side of the scintillator element.

Between the collimator 20 and the reflector material 15 at the upper side of the scintillator elements 3 or the upper side of the scintillator element 3 is located an optical element 13. Next to the optical element 13 and to the side are located light sources 9. The light from the light sources 9 can uniformly illuminate the scintillator elements 3 with the aid of the optical element 13. The optical element 13 can be formed, for example, as a diffusor or by lenses.

A light-impermeable housing 11 surrounds the collimator 20, the light sources 9, the optical element 13, the scintillator elements 3 and the reflector material 15, the first photodiodes 5 and the electronic evaluation device 7. The light-impermeable housing 11 can be in one part or in several parts. The light-impermeable housing 11 shields the interior substantially from external light effects. The light sources 9 can emit a defined quantity of light. A portion of the defined quantity of light can penetrate the opening in the reflector material 15. The defined quantity of light can be used for illumination of the scintillator elements 3 to establish a predetermined state of the scintillator element 3 or to ascertain the state of the scintillator element 3.

FIG. 3 shows an example embodiment of an inventive detector 1 having the second photodiode 17. A detection element 3, 15, 5, 7 comprises a scintillator element 3 which is at least partially covered at the upper side and the side surfaces by a reflector material 15. A different reflector material 15 can also be used at the upper side and the side surfaces.

The reflector material 15 has at least one opening at the upper side of the scintillator element 3 to ensure illumination of the scintillator element 3. For example, in the case of a scintillator element 3 which has a scintillator material having a high light yield, for example CsI, a very large opening of the reflector material 15 can be used at the upper side of the scintillator element 3 or the reflector material 15 can even be dispensed with at the upper side of the scintillator element 3. Even with scintillator materials having, for example, a lower light yield a structuring of the reflector material 15 can be used at the upper side of the scintillator element.

A second photodiode 17 can be located next to the first photodiode 5. The second photodiode 17 is incorporated, for example, by the same substrate and the first photodiode 5 and the second photodiode 17 can be identical in construction. The second photodiode 17 is not located below a scintillator element 3 but next to the first photodiode 5. The second photodiode 17 is directly illuminated, or illuminated with the aid of the optical element 13, by the light source 9. The second photodiode 17 can be protected, for example by a shield (not shown) from incident X-ray radiation. Filters (not shown) can be used upstream of the second photodiode 17.

Between the collimator 20 and the reflector material 15 at the upper side of the scintillator elements 3 or the upper side of the scintillator element 3 is located an optical element 13. Next to the optical element 13 and to the side are located light sources 9. The light from the light sources 9 can uniformly illuminate the scintillator elements 3 and the second photodiode 17 with the aid of the optical element 13. The optical element 13 can be formed, for example, as a diffusor or by lenses.

A light-impermeable housing 11 surrounds the collimator 20, the light sources 9, the optical element 13, the scintillator elements 3 and the reflector material 15, the first photodiodes 5, the second photodiode 17 and the electronic evaluation device 7. The light-impermeable housing 11 can be in one part or in several parts. The light-impermeable housing 11 shields the interior substantially from external light effects.

The light sources 9 can emit a defined quantity of light. A portion of the defined quantity of light can penetrate the opening in the reflector material 15. The defined quantity of light can be used for illumination of the scintillator elements 3 to establish a predetermined state of the scintillator element 3 or to ascertain the state of the scintillator element 3. The second photodiode 17 can be used to control the reproducibility of the defined quantity of light. The second photodiode is subject to the same material properties and the same temperature conditions as the first photodiode 5.

FIG. 4 shows an example embodiment of an inventive detector 1 having light sources 9 integrated in the electronic evaluation device 7. A detection element 3, 15, 5, 7 comprises a scintillator element 3 which is covered at the upper side and the side surfaces by a reflector material 15. A different reflector material 15 can also be used at upper side and the side surfaces. The light source 9 is integrated in the electronic evaluation device 7, for example as an LED. The light sources 9 can each be arranged below and between the scintillator elements 3, so they can illuminate both adjoining scintillator elements.

A light-impermeable housing 11 surrounds the collimator 20, the light sources 9, the optical element 13, the scintillator elements 3 and the reflector material 15, the first photodiodes 5 and the electronic evaluation device 7. The light-impermeable housing 11 can be in one part or in several parts. The light-impermeable housing 11 shields the interior substantially from external light effects. The light sources 9 can emit a defined quantity of light. The defined quantity of light can be used for illumination of the scintillator elements 3 to establish a predetermined state of the scintillator element 3 or to ascertain the state of the scintillator element 3.

In a further embodiment (not shown) a second photodiode 17 can also be used without structuring of the reflector material 15 at the upper side of the scintillator element 3 or with an integrated light source 9 in the electronic evaluation device 7.

FIG. 5 shows an example embodiment of an inventive method for ascertaining a state of the scintillator element. In the step of illumination 21 the scintillator element 3 is illuminated by a light source 9. The scintillator element 3 is illuminated with a defined quantity of light. In the step of determination 23 the transmission of the defined quantity of light or the luminescence excited by the defined quantity of light is determined with the aid of first photodiode 5. The state of the scintillator element 3 is therefore ascertained in respect of its transmission or luminescence. Following this the correction variables for correcting the scan values or correcting the calibration tables can be determined in step 25.

In step 27 a scan is performed with X-ray radiation and the determined correction, for example a correction variable or the correction of the calibration tables, can be applied to the scan values. The correction can be made before, during or after the scan. For example, the correction can be made before the scan with the aid of adjustment of an amplification. The correction during the scan can occur, for example, by using the corrected calibration tables, for example by way of a corrected adjustment of a digital-to-analogue converter during the evaluation of the scan signal in the electronic evaluation device.

Illumination 21 and determination 23 are carried out in radiation-free periods or in scanning breaks. Illumination 21 and determination 23 can be carried out, for example, before or after calibration using X-ray radiation to ascertain the state of the scintillator element 3 before and after calibration using X-ray radiation. In scanning breaks or radiation-free periods the luminescence or transmission of the scintillator material is determined and compared with the values before or after calibration using X-ray radiation.

In the case of deviations a correction variable for correcting the scan values or a correction of the calibration tables can be determined in step 25 with the aid of the ascertained values of the transmission or luminescence. The correction variable for correcting the scan values or a correction of the calibration tables from step 25 is used before, during or after the subsequent scan in step 27. The duration of illumination 21 with the defined quantity of light is chosen at least such that a reliable value for the transmission or luminescence can be ascertained. The duration of illumination 21 can be, for example, a few milliseconds.

Figure 6:
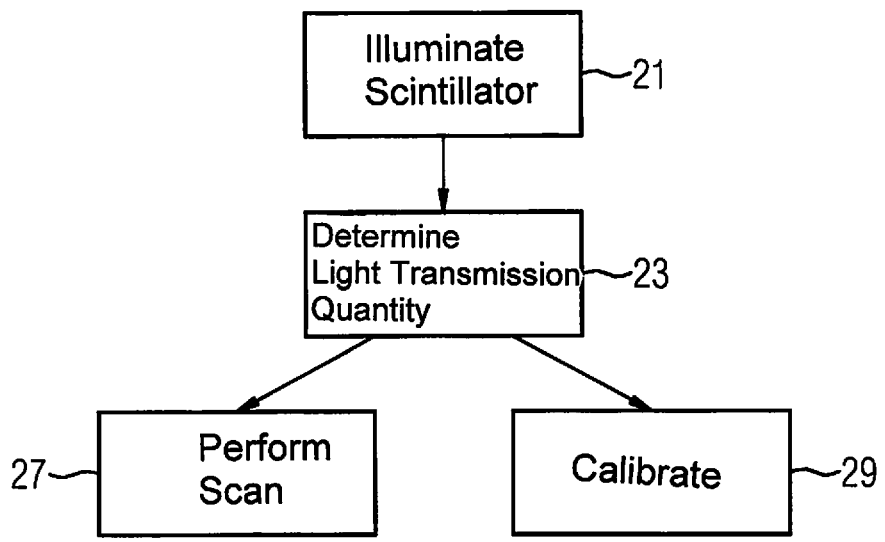
FIG. 6 schematically shows a diagram of an embodiment of an inventive method for establishing a state of the scintillator element.

FIG. 6 shows an example embodiment of an inventive method for establishing a state of the scintillator element. In the step of illumination 21 the scintillator element is illuminated before a scan with X-ray radiation, or before a calibration using X-ray radiation, with a defined quantity of light.

A predetermined state of the scintillator element is established thereby, and this is called the step of determination 23. The predetermined state of the scintillator element corresponds to a state which in respect of polarization, transmission or luminescence corresponds to the state which is established following irradiation with X-ray radiation. The light source 9 is therefore chosen to be so strong that the luminescence generated by the light source is comparable to the luminescence attained under X-ray radiation. The wavelength of the light source 9 is preferably in the ultraviolet range. The predetermined state corresponds to a saturated state, i.e. the state does not substantially change under additional or subsequent irradiation with X-ray radiation.

Calibration using X-ray radiation is carried out in step 29 while the scintillator element 3 is in the predetermined state. The scan with X-ray radiation, for example for the purpose of imaging, is carried out in alternative step 27. The scintillator element 3 is in the predetermined state, wherein this also corresponds to the state of the scintillator element 3 during calibration. A change in the detector response can be prevented thereby and corrections can be prevented in step 27.

Figure 7:
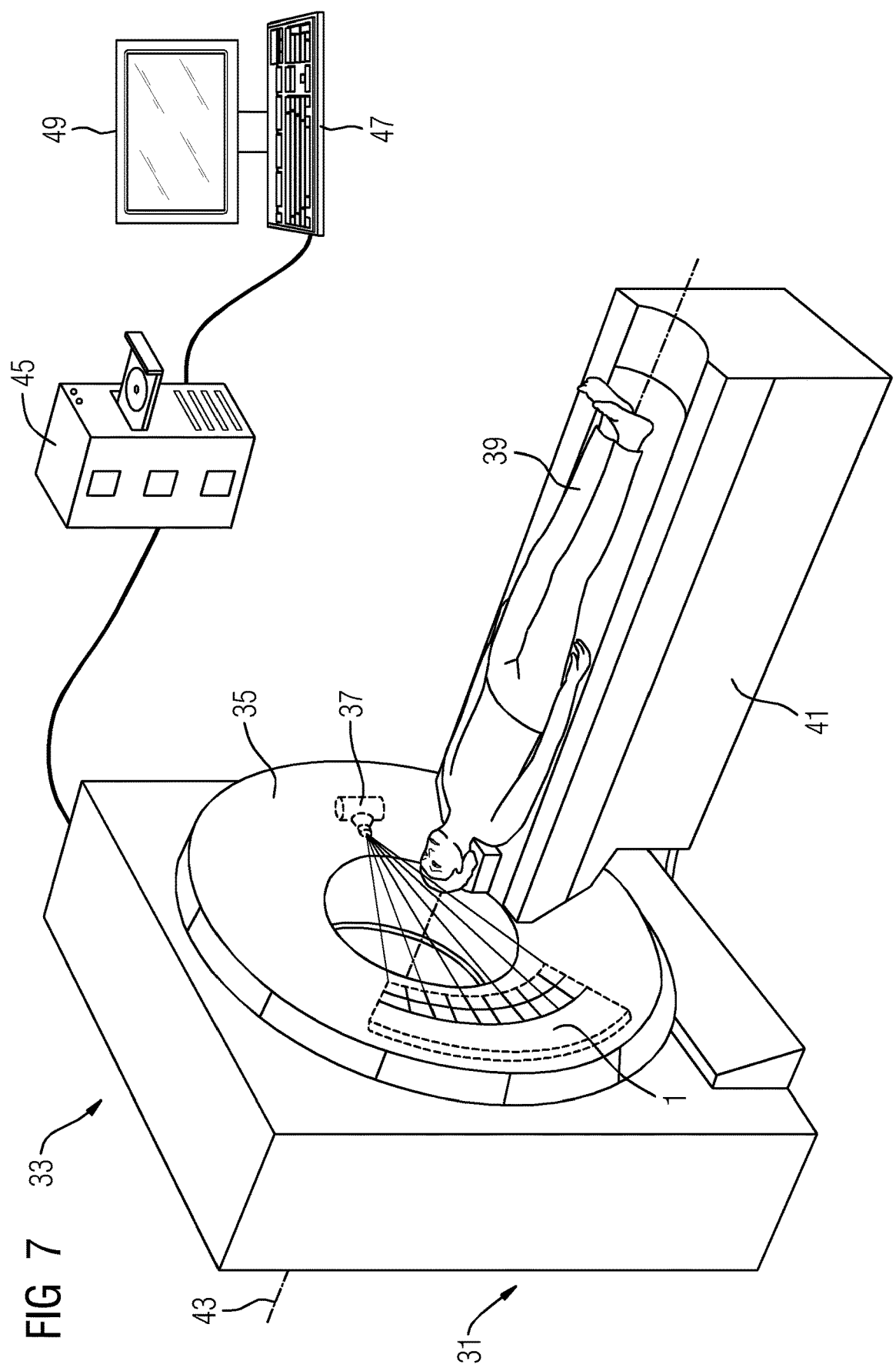
FIG. 7 schematically shows a diagram of an embodiment of an inventive computer tomograph.

FIG. 7 shows an example embodiment of an inventive computer tomograph 31 having an inventive detector 1. The computer tomograph 31 includes a gantry 33 having a rotor 35. The rotor 35 comprises an X-ray source 37 and the inventive detector 1. The patient 39 is positioned on the examination table 41 and can be moved along the axis of rotation z 43 through the gantry 33. An arithmetic unit 45 is used for controlling and calculating the slice images. An input device 47 and an output device 49 are connected to the arithmetic unit 45.

Although the invention has been illustrated in detail by the preferred example embodiment, it is not limited by the disclosed examples and a person skilled in the art can derive other variations herefrom without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A detector for detecting at least one of X-ray and gamma radiation, comprising:
    a scintillator element to convert the at least one of X-ray and gamma radiation into light, wherein the scintillator element includes at least one side surface, an upper side and a lower side;
    a first photodiode on the lower side of the scintillator element;
    an electronic evaluation device;
    a light source, designed to illuminate the scintillator element with a defined first quantity of light; and
    a light-impermeable housing that houses the scintillator element, the first photodiode, the electronic evaluation device and the light source, wherein
        the light source is configured to excite luminescence by way of irradiation with the defined first quantity of light of the scintillator element,
        the first photodiode is configured to ascertain a second quantity of light that is a portion of the defined first quantity of light; and
        the first photodiode is connected to the electronic evaluation device configured to perform an evaluation of the second quantity of light ascertained by the first photodiode and determine, in respect of the luminescence, a correction variable.

2. The detector of claim 1, wherein the light source is designed to emit photons from the light source including a wavelength less than an excitation wavelength of the scintillator element.

3. The detector of claim 2, wherein the light source is designed to emit photons including a wavelength detectable by the first photodiode.

4. The detector of claim 2, further comprising an optical element for uniform illumination of at least one section of the scintillator element.

5. The detector of claim 2, wherein the light source is integrated in the electronic evaluation device.

6. The detector of claim 2, further comprising a second photodiode, wherein the second photodiode is illuminatable by the light source.

7. A medical device comprising the detector of claim 2.

8. The medical device of claim 7, wherein the medical device is a computer tomograph.

9. The detector of claim 1, wherein the light source is designed to emit photons including a wavelength detectable by the first photodiode.

10. The detector of claim 9, further comprising an optical element for uniform illumination of at least one section of the scintillator element.

11. The detector of claim 1, further comprising an optical element for uniform illumination of at least one section of the scintillator element.

12. The detector of claim 11, further comprising a filter between the scintillator element and the first photodiode, the filter being impermeable for a wavelength of the light source.

13. The detector of claim 1, further comprising a filter between the scintillator element and the first photodiode, the filter being impermeable for a wavelength of the light source.

14. The detector of claim 1, wherein the light source is arranged such that the upper side or the lower side of the scintillator element is illuminatable.

15. The detector of claim 1, wherein at least one of the at least one side surface and the upper side of the scintillator element is at least partially covered by a reflector material applied to at least one of the at least one side surface and the upper side of the scintillator element.

16. The detector of claim 1, wherein the light source is integrated in the electronic evaluation device.

17. The detector of claim 1, further comprising a second photodiode adjacent the first photodiode, wherein the first photodiode is directly beneath the scintillator element and the second photodiode is identical to the first photodiode and is not directly beneath the scintillator element and is illuminatable by the light source.

18. The detector of claim 17, wherein the second photodiode is connected to an evaluation device.

19. The detector of claim 1, further comprising a controller to control the light source to emit a defined quantity of light.

20. The detector of claim 1, wherein the first photodiode is connected to an evaluation device.

21. A medical device comprising the detector of claim 1.

22. The medical device of claim 21, wherein the medical device is a computer tomograph.

23. A detector for detecting at least one of X-ray and gamma radiation, comprising:

a scintillator element to convert the at least one of X-ray and gamma radiation into light, wherein the scintillator element includes at least one side surface, an upper side and a lower side;

a first photodiode on the lower side of the scintillator element;

an electronic evaluation device; and a light source, designed to illuminate the scintillator element with a defined first quantity of light, wherein the light source is configured to emit photons including a wavelength detectable by the first photodiode and less than an excitation wavelength of the scintillator element, the first photodiode is configured to ascertain a second quantity of light that is a measure of transmission of the scintillator element, the second quantity of light being a portion of the defined first quantity of light used for illumination of the scintillator element which is registered by the first photodiode, and the first photodiode is connected to the electronic evaluation device, configured to perform an evaluation of the second quantity of light ascertained by the first photodiode and determine, in respect of detected luminescence, a correction variable.

* * * * *